United States Patent
Sullivan

(10) Patent No.: US 6,225,506 B1
(45) Date of Patent: May 1, 2001

(54) SYNTHESIS OF ALKENE-2-ONES

(75) Inventor: Jeffrey M. Sullivan, Loveland, CO (US)

(73) Assignee: Boulder Scientific Company, Mead, CO (US)

( * ) Notice: Subject to any disclaimer, the term of this patent is extended or adjusted under 35 U.S.C. 154(b) by 0 days.

(21) Appl. No.: 09/459,458

(22) Filed: Dec. 13, 1999

(51) Int. Cl.⁷ .................................................. C07C 45/88
(52) U.S. Cl. .............................................................. 568/393
(58) Field of Search ............................................. 568/393

(56) References Cited

U.S. PATENT DOCUMENTS 3,983,175 * 9/1976 Tamai et al. .
4,602,117 * 7/1986 Lantzch .

* cited by examiner

*Primary Examiner*—Johann Richter
*Assistant Examiner*—Sikarl A. Witherspoon
(74) *Attorney, Agent, or Firm*—Edward S. Irons

(57) ABSTRACT

A method for synthesizing an alkyl-2-one by reacting a 2-alkene halide with a 2,4-alkanedione in an alkylene glycol medium having a boiling point higher than said alkene-2-one is described.

4 Claims, No Drawings

SYNTHESIS OF ALKENE-2-ONES

FIELD OF THE INVENTION

This invention relates to the synthesis of alkene-2-ones. More particularly, the invention relates to the synthesis of 5-hexen-2-one.

BACKGROUND OF THE INVENTION

It is known to produce 5-methyl-5-hexen-2-one by the reaction of 2,4-pentanedione methallyl chloride in ethanolic potassium carbonate. Boatman, S., et al, *Org. Synth.* Coll. Vol. 5:767–768. The comparative boiling points of the product and the ethanol solvent may preclude direct distillate of the product from the reaction mixture. Yields of 47% to 52% have been reported.

SUMMARY OF THE INVENTION

Pursuant to this invention, 2,4-alkane diones are converted to alkene-2-ones by treating with a 2-alkene halide in the presence of an alkylene glycol which has a boiling point higher than the boiling point of the alkene-2-one product. The use of glycol instead of ethanol as in the prior art eliminates the need for aqueous quenching and phase extraction, and facilitates the direct distillation of low boiling alkene-one products from the higher boiling ethylene glycol, wherein a true "one pot" procedure with direct distillation of the product from the reaction mixture is provided.

GENERAL DESCRIPTION OF THE INVENTION

The invention is generally illustrated by the equation:

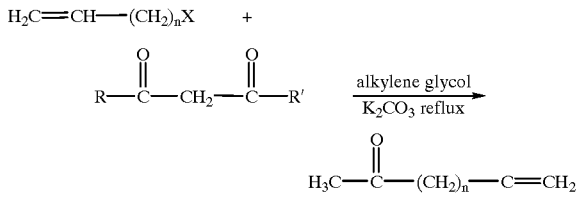

wherein X is a halogen, R and R' are alkyl groups, preferably $C_1$ to $C_{10}$ alkyl groups, which may be identical or different, and n is 1 to 4. The boiling point of the alkylene glycol is below that of the alkene-2-one product.

The reactants and the alkylene glycol are selected to provide a reaction mixture from which the desired product may be distilled directly. Preferably, equimolar amounts of alkane dione and 2-alkene halide are used. An initial reaction temperature in the range of about 20° C. to about 40° C. is appropriate. The temperature is then preferably raised to about 60° C. to about 90° C. after a time period of one or two hours to complete the reaction.

Pursuant to a preferred embodiment of the invention, allyl chloride is reacted with acetylacetone and $K_2CO_3$ in an ethylene glycol medium to produce 5-hexen-2-one.

EXAMPLE 1

Laboratory 276 grams (3 mol) of allyl chloride and 306 grams (3 mol) of pentanedione was added to 1.2 liters of ethylene glycol in a 2 liter flask set up for reflux. After initiation of vigorous stirring, 414 grams (3 mol) of $K_2CO_3$ was added in three portions over 15 minutes. When the $K_2CO_3$ addition was completed, the mixture was slowly heated to avoid allyl chloride distillation. Over two hours, the pot temperature was gradually increased from 20° C. to 40° C. Over the next two hours, the pot temperature was increased from 40° C. to 80° C. Thereafter, all volatile compounds were removed by distillation up to a pot temperature of 140° C.

Yield: crude 5-hexane-2-one; 90%. Distilled yield: 241 g.; 2.46 mol; 82%. Distilled yield upon repetition of this experiment: 238 g; 2.44 mol; 80%.

COMPARATIVE EXAMPLE 1(a)

Preparation of 5-hexen-2-one Using MeOH as solvent

A 2 liter flask is charged with 220 g (2.2 mol) of 2,4-pentanedione, 320 g (2.32 mol) of potassium carbonate, 1 liter of methanol, and 152.8 g (2.0 mol) of allyl chloride. The mixture is heated to 40–45° C. for 16–18 hours, and heated to reflux (56° C.) for 2–3 hours. The condenser is replaced by a distilling head, and the bulk of the methanol is distilled from the mixture to a pot temperature of 66° C. Water (100 mL) is added, and the mixture is extracted three times with ether. The combined ether extracts are dried over anhydrous sodium sulfate and filtered. The solvent is evaporated. The residue is distilled through a 6 inch Vigreaux column using 25–30 mm Hg vacuum to afford 39 g of 5-hexen-2-one. Yield: 20%.

COMPARATIVE EXAMPLE 1(b)

Preparation of 5-hexen-2-one Using MeOH as Solvent and Non-aqueous Work-up

Example 1(a) was repeated. After removal of the methanol by distillation, the mixture was diluted with ether and filtered. The ether is evaporated. The residue is distilled through a 6 inch Vigreaux column using 68 mm Hg vacuum to afford 58.9 g of 5-hexen-2-one. Yield: 30%.

EXAMPLE 2

Pilot Plant

Pilot Plant Process General Description

Ethylene glycol, potassium carbonate, allylchloride, and acetylacetone are added to a vessel. The vessel is heated to 40° C. and held for 1 hour, and then heated to reflux for several hours with carbon dioxide gas evolution. Solvents are then removed by distillation, and the crude product is drummed. The crude product is fractionally distilled by collecting a forecut atmospherically end product under rough pump vacuum.

Pilot Plant Procedure 455 lbs. of ethylene glycol are charged to a reactor. 131.9 lbs. of potassium carbonate are added, with agitation, to the ethylene glycol in the reactor. The pot temperature is not permitted to exceed 30° C. 83.6 pounds of 2,4 pentanedione (acetylacetone) are added to the reactor. The pot pressure is not permitted to exceed 10 psig. The contents of the reactor are heated to a temperature of 40–45° C. and held at that temperature for 1 hour. Thereafter, the pot temperature is raised to the range of 60–80° C. under reflux for 4–5 hours. The psig is not permitted to exceed 10. The reaction mixture is cooled under nitrogen to 20–25° C. Solvents are distilled from the reaction mixture at a pot temperature of 100–140° C. Upon completion of the distillation, the pot temperature is reduced to 20–25° C. under 2–5 psig nitrogen. Distilled yield: 60%.

EXAMPLE 3
Synthesis of 5-Hexen-2-One
Reaction 378.5

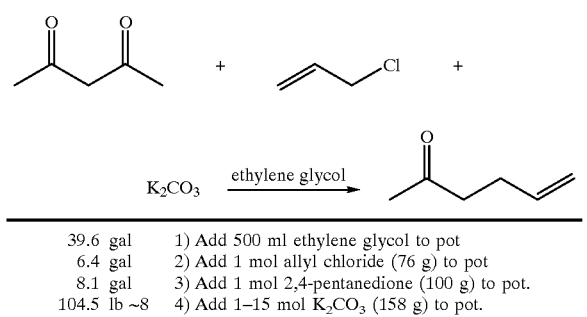

| | |
|---|---|
| 39.6 gal | 1) Add 500 ml ethylene glycol to pot |
| 6.4 gal | 2) Add 1 mol allyl chloride (76 g) to pot |
| 8.1 gal | 3) Add 1 mol 2,4-pentanedione (100 g) to pot. |
| 104.5 lb ~8 | 4) Add 1–15 mol $K_2CO_3$ (158 g) to pot. |

Method

1) Heat to reflux with vigorous stirring. Reflux begins at 42–45° C. pot.

2) Reflux 4 hours. As allyl chloride is consumed in the reaction, the reflux temperature increased to 80° C.

3) After 4 hours, cool pot to 20° C. Change to distillation.

4) Under rough pump, heat reaction mixture to distill all volatile products to pot T=140° C. head T=120° C.

5) Dry with $Na_2SO_4$.

6) Fractionally distill product. 118–122° C. 5:1 reflux:return.

Note

1) During reflux do not vent the pot because an appreciable loss of allyl chloride will occur. Cool condenser with "chiller", if necessary.

2) During distillation of reaction mixture, cool receiver pot and use "chiller" on condenser.

Yield: Crude 65–70% Distilled 50%

EXAMPLE 3(a)

When the Example 3 reaction was scaled to fit in a 100 gallon pot and run in the pilot plant, a 60% distilled yield was obtained.

I claim:

1. A method for the synthesis of an alkene-2-one which comprises:

(i) treating a 2-alkene halide with a 2,4 alkanedione in alkylene glycol medium,
      wherein said alkylene glycol medium boiling point is higher than the boiling points of said alkene-2-one; and
      wherein a reaction mixture containing said alkene-2-one is produced;

(ii) recovering said alkene-2-one by direct distillation from said reaction mixture
      wherein said distillation is accomplished at a temperature below the boiling point of said alkylene glycol.

2. The claim 1 method, wherein said 2-alkene halide is allylchloride, said alkanedione is 2,4 hexanedione, and said alkylene glycol is ethylene glycol.

3. A method for synthesizing 5-hexen-2-one, which comprises:

(i) providing a reactor containing a reaction mixture comprising allyl chloride, 2,4-pentanedione, potassium carbonate and ethylene glycol, (ii) heating said reaction mixture in said reactor to a pot temperature of from about 20° C. to about 40° C. for a time period effective to produce a substantial but incomplete reaction of said allyl chloride with said 2,4-pentanedione;

(iii) thereafter raising said pot temperature to about 60° C. to about 80° C. to substantially complete said reaction of allyl chloride with 2,4-pentanedione
      wherein a reaction mixture comprising said 5-hexen-2-one and said glycol is produced in said reactor; and (iv) separating said 5-hexen-2-one by distillation from the reaction mixture.

4. The method of claim 3 wherein said step (i) reaction mixture comprises allyl chloride and 2,4-pentanedione in about stoichiometric proportions.

* * * * *